United States Patent
Govari et al.

(10) Patent No.: US 11,900,524 B2
(45) Date of Patent: Feb. 13, 2024

(54) CONSTRUCTING TOPOGRAPHY OF LUMEN WALL IN 4D ULTRASOUND IMAGE WITH VIRTUAL ELLIPSOID OR POLYHEDRON

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/685,855

(22) Filed: Mar. 3, 2022

(65) Prior Publication Data

US 2023/0281911 A1    Sep. 7, 2023

(51) Int. Cl.
G06T 15/08    (2011.01)
G06T 19/20    (2011.01)
A61B 8/08    (2006.01)

(52) U.S. Cl.
CPC .......... *G06T 15/08* (2013.01); *A61B 8/0883* (2013.01); *A61B 8/483* (2013.01); *G06T 19/20* (2013.01); *G06T 2200/04* (2013.01); *G06T 2210/21* (2013.01); *G06T 2210/41* (2013.01); *G06T 2219/2004* (2013.01); *G06T 2219/2012* (2013.01); *G06T 2219/2016* (2013.01)

(58) Field of Classification Search
None
See application file for complete search history.

(56) References Cited

U.S. PATENT DOCUMENTS 6,332,089 B1    12/2001    Acker et al.
6,618,612 B1    9/2003    Acker et al.
(Continued)

FOREIGN PATENT DOCUMENTS

WO    WO9605768    2/1996

OTHER PUBLICATIONS

Bernardini et al., "The Ball-Pivoting Algorithm for Surface Reconstruction", Oct.-Dec. 1999, IEEE Transactions on Visualization and Computer Graphics, vol. 5, No. 4, pp. 349-359 (Year: 1999).*
(Continued)

*Primary Examiner* — Kent W Chang
*Assistant Examiner* — Jonathan M Cofino
(74) *Attorney, Agent, or Firm* — Gabriel K. Azar

(57) ABSTRACT

A method includes receiving a 3D image of a portion of an organ including a cavity, the image comprising voxels having respective values. A wall of the cavity is identified in the image, by (i) positioning virtual solid objects inside respective sub-volumes of the cavity, (ii) moving the virtual solid objects inside the cavity according to a predefined rule of motion, (iii) while the virtual solid objects move inside the cavity, adapting the traversed voxels to predefined value indicative of the interior of the cavity, (iv) responsively to detecting that a virtual solid object comes into contact with the wall, rolling the virtual solid object over the wall, and adapting a surface of the virtual solid object with the values of the voxels over which the surface rolls, and (v) converting adapted voxel values that are lower than a threshold voxel value into the predefined value indicative of the interior.

26 Claims, 4 Drawing Sheets

(56) References Cited

U.S. PATENT DOCUMENTS

| | | |
|---|---|---|
| 6,968,299 B1 | 11/2005 | Bernardini et al. |
| 10,376,320 B2 | 8/2019 | Harlev et al. |
| 2002/0065455 A1 | 5/2002 | Ben-Haim et al. |
| 2003/0120150 A1 | 6/2003 | Govari |
| 2003/0147556 A1 | 8/2003 | Gargesha et al. |
| 2004/0068178 A1 | 10/2004 | Chang et al. |
| 2005/0131660 A1* | 6/2005 | Yadegar .................. G06T 9/002 375/240 |
| 2007/0081702 A1* | 4/2007 | Porat ........................ G06T 7/12 382/128 |
| 2011/0152684 A1* | 6/2011 | Altmann .............. A61B 8/5238 600/443 |
| 2011/0206253 A1* | 8/2011 | Averbuch ................ G06T 7/187 382/128 |
| 2013/0009957 A1* | 1/2013 | Arakita ................ H04N 13/117 345/424 |
| 2017/0325891 A1* | 11/2017 | Harlev ................... A61B 34/25 |
| 2018/0049718 A1 | 2/2018 | Schneider et al. |
| 2019/0009473 A1* | 1/2019 | Morovic ................. G06T 17/00 |
| 2020/0211280 A1 | 7/2020 | Cohen et al. |
| 2020/0368616 A1* | 11/2020 | Delamont ............. A63F 13/213 |

OTHER PUBLICATIONS

International Search Report dated May 12, 2023 from corresponding PCT Application No. PCT/IB2023/050906.

* cited by examiner

CONSTRUCTING TOPOGRAPHY OF LUMEN WALL IN 4D ULTRASOUND IMAGE WITH VIRTUAL ELLIPSOID OR POLYHEDRON

FIELD OF THE DISCLOSURE

The present disclosure relates generally to image processing, and particularly to image processing of ultrasound images.

BACKGROUND OF THE DISCLOSURE

Techniques to generate a visual representation of a portion of an organ have been previously proposed in the patent literature. For example, U.S. Pat. No. 10,376,320 describes devices, systems, and methods directed to generating three-dimensional surface representations of an anatomic structure such as a heart cavity. More specifically, a three-dimensional surface representation of the anatomic structure is constrained relative to one or more anchor portions corresponding to received input regarding the location of anatomic features of the anatomic structure. To this end, the three-dimensional surface representation can be extracted from the three-dimensional data structure according to any one or more computational algorithms known in the art for volumetrically smoothing three-dimensional representations of objects including a "ball-pivoting" algorithm, a "power crust" algorithm, and other similar algorithms. The resulting three-dimensional surface representation includes salient features of the anatomic structure and, therefore, can be useful as visualization tool during any of various different medical procedures, including, for example, cardiac ablation.

As another example, U.S. Patent Application Publication 2020/0211280 describes image processing that is carried out by accepting an array of voxels that include data representing a physical property of a 3-dimensional object, segmenting the array of voxels into a plurality of regional subarrays of voxels that respectively satisfy predetermined criteria, transforming the subarrays into respective triangular meshes, the meshes having triangles that surround the subarrays and intercept the outer voxels of the subarrays, and rendering the triangular meshes on a display. In one example, the processor uses the Ball-Pivoting Algorithm (BPA) to produce the mesh. Typically, if the BPA is used, a size of the ball is set to correspond to the size of the voxels referred to above.

The present disclosure will be more fully understood from the following detailed description of the examples thereof, taken together with the drawings in which:

DETAILED DESCRIPTION OF EXAMPLES

Overview

Figure 1:
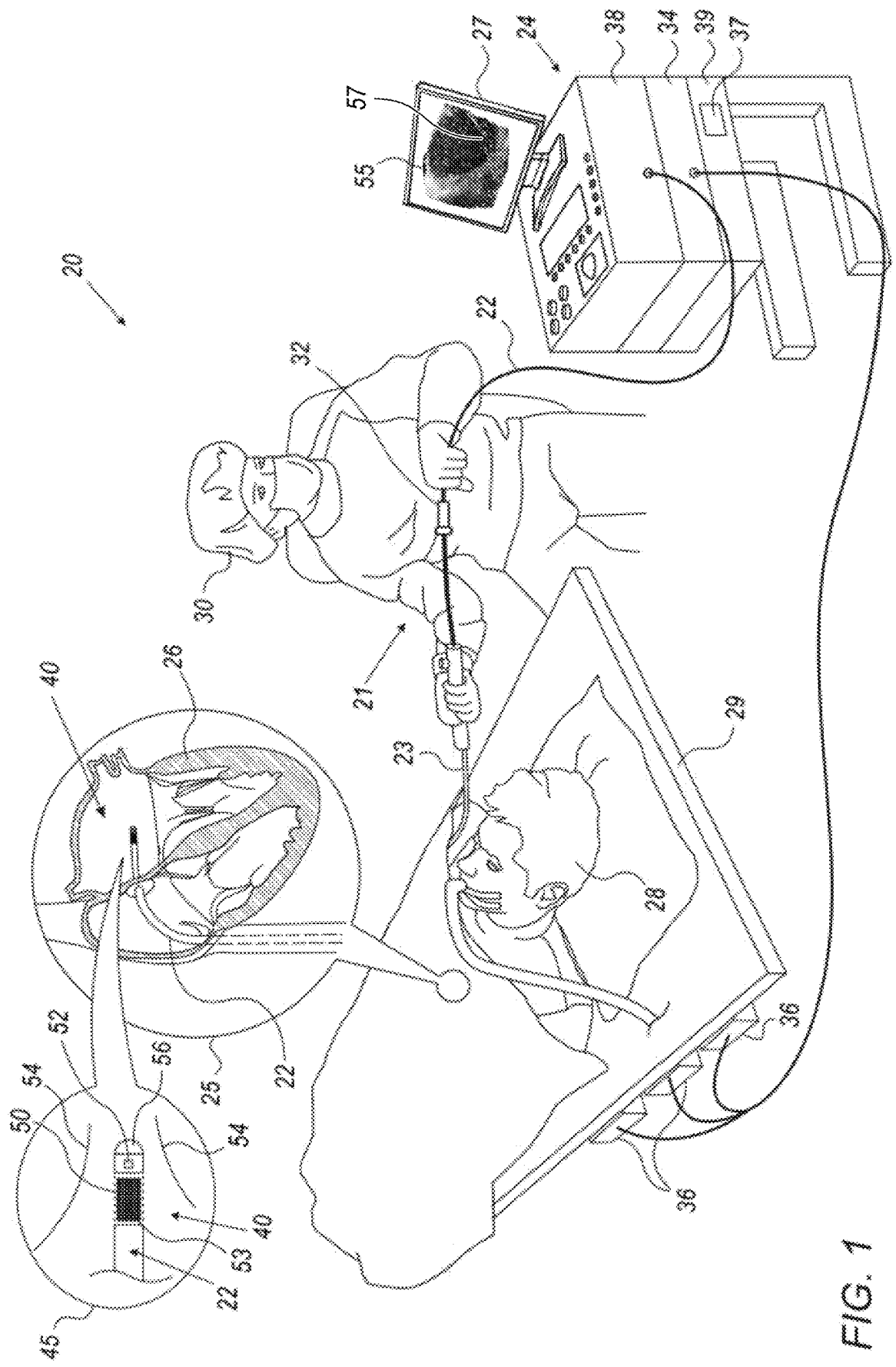
FIG. 1 is a schematic, pictorial illustration of a catheter-based system configured to perform 4D ultrasound imaging of a cardiac cavity, in accordance with an example of the present disclosure.

Three-dimensional (3D) or four-dimensional (4D) ultrasound images of an organ may be acquired noninvasively or by a probe, such as a catheter, with a two-dimensional (2D) array of ultrasound transducers. In the present context, the term "3D ultrasound image" refers to an ultrasound image that represents a certain volume in three dimensions. The term "4D ultrasound image" refers to a time series of 3D ultrasound images of a certain volume. A 4D image can be regarded as a 3D movie, the fourth dimension being time. Another way of describing a 4D image (or rendering) is as a time-dependent 3D image (or rendering).

A physician often wants to inspect a tissue wall of a cavity (e.g., a lumen) of the organ in the 3D image in order to delineate the lumen wall captured in the image and present the delineated lumen wall. Optionally, a model (or a surface) of the lumen may be constructed based on the delineation for display to the physician. If the lumen of the organ is empty, or filled with liquid, it may be easy to distinguish between voxels (image voxels) belonging to tissue of the lumen wall and voxels belonging to the volume in the lumen. However, if the lumen is filled with blood (or other material), the blood (or other material) may also appear gray, and the delineation may be difficult, e.g., the blood (or other material) may add noise to the image. The problems are intensified in cardiac images because of the movement of blood and of the heart chambers being imaged.

Examples of the present disclosure that are described herein provide methods and systems applied to medical images, such as 3D ultrasound images, to construct a cavity of an organ by finding cavity voxels (blood voxels in case of a cardiac cavity) and thereafter setting the cavity voxels with a predefined cavity voxel value (e.g., given a Hounsfield unit (HU) value viewed as black in an ultrasound image) that is easily distinguishable from wall tissue voxel values. The result is a clear delineation (e.g., in a 3D ultrasound rendering) of the cavity wall tissue of an organ displayed to the physician, including those in heart chambers.

In some examples, an algorithm is provided that is applied by a processor to analyze a 3D image by first creating a virtual solid object, such as an ellipsoid (e.g., a virtual ball), or a virtual polyhedron (e.g., a virtual cube), inside the cavity. The processor moves the virtual object in a cavity volume using motion laws described below. When engaging a surface, for example, the object rolls around the surface and/or bounces off the surface, so as to gradually construct the surface of the lumen wall.

Since the surface of an organ cavity, such as a cardiac chamber of the heart, is typically curved, in some cases an ellipsoid is a good choice of a shape for tracing the surface. The dimensions of the ellipsoid, such as the diameter of a ball, can be defined based on the desired resolution and the expected geometry of the organ. In other cases, e.g., to geometrically best fit a virtual object shape to the 3D image voxels, the processor creates a virtual cube that can be as small as a single voxel. The virtual cube, moving in a cavity volume when engaging a surface, "rolls" facet by facet around the 3D image to construct (e.g., voxel by voxel) the surface of the lumen wall in a similar manner, mutatis mutandis, as that done using a ball. In some examples, another virtual object shape may be found most suitable, such as of a polyhedron with triangular facets (e.g., an icosahedron).

In an example, the processor starts a cavity construction process by positioning the virtual ball (or polyhedron) in a sub-volume that is completely within a volume known to be the internal lumen of the cavity (i.e., not touching a wall). The sub-volume is known to be such, for example, from its voxel values that correspond to a black color of the fully immersed sub-volume.

As the ball (or polyhedron) rolls, the processor adapts the pixel values (e.g., colors) of the surface of the ball (or polyhedron) to the voxel values of the organ inner wall that the ball is touching. At first the surface of the ball is completely black, since it is in a completely black volume. The rolling path may begin as a random, pseudo-random, or planned path. Continuing the description with a ball, by way of example, the rolling ball adapts its surface color to the colors of the voxels it touches, e.g., the surface of the virtual ball is "painted" with the image voxel values that it touches. The following steps are taken:

If the entire surface of the ball is black, the ball is situated in a portion of the 3D image that represents the lumen. The processor continues to move the ball and check the colors.

If the ball surface (or part thereof) includes dispersed speckles of gray or white that do not form a continuous blob, the part of the ball that includes the dispersed speckles is still considered to be situated in a portion of the 3D image that represents the lumen. The speckles are typically the result of blood flowing through the lumen. The processor accordingly changes all of the image voxels at that location to black. This cleans the speckle noise due to the blood flow. The processor continues to move the ball and check the colors.

If part of the surface of the ball includes a patch of white/gray, the processor regards the patch as part of the tissue wall. The boundary is defined by setting a threshold value such that a voxel value larger than the threshold means that the voxel is part of the cavity wall tissue. For example, the threshold voxel value may correspond to a color of a continuous bulb of predefined size of cavity wall tissue. The processor marks those image voxels as the tissue wall (using white or some other color).

In one example, the ball rolls in random directions, while in another example the ball mat roll in pseudo-random way, so to minimize chances the ball repeating its track.

Once colors on the ball have been checked, the processor may start rolling a clean ball, and so on, until all surface voxels are accounted for. In this example, the processor has any moved-through cavity voxels adapting a predefined cavity voxel value (e.g., a color black). This creates a black shell surrounding a reduced cavity. Next, the processor turns the color of each voxel of the reduced cavity into a value indicative of the interior, such the color black (i.e., converts values of all cavity voxels inner to shell to the cavity voxel value), thereby achieving a fully distinct black cavity interfaced with a clearly delineated cavity wall surface.

In another example, once colors on the ball have been checked, the processor changes the direction of the ball so that it bounces off of the detected tissue wall. Also in this example, the processor has any moved-through cavity voxels adapting a predefined cavity voxel value (e.g., a color black). However, the cavity color is formed between steps in which the processor starts rolling a clean ball in wall tissue location. As the ball bounces around, both a surface of the tissue wall and cavity color are defined. The bouncing path may begin as a random, or pseudo random, e.g., into a backwards semi-hemisphere distribution of directions. Alternatively, the bouncing path may be along a planned path or one governed by a physical rule (e.g., specular reflection). Note that any physical rule used by the algorithm need not reflect an exact physical low of motion. For example, the processor may retain a specular direction of bouncing back despite the ball already rolled away from location it encountered wall tissue.

In yet another example, the positions the ball in a volume that is completely black or in a volume that is known to be a lumen. The surface of the ball just bounces between cavity walls and adapts the colors that it is touching. At first the surface of the ball is completely black. The bouncing path may begin as a random, pseudo random, planned path or one governed by a physical rule (e.g., specular reflection). As the ball moves hits a cavity wall location it updates is surface color to adapt to the colors that it is hitting, e.g., the surface of the virtual ball is "painted" with the image voxel values that it is hitting. The colors are compared to threshold, described as above. At a same time, the processor has any moved-through cavity voxels adapting a predefined cavity voxel value (e.g., a color black).

The process continues until all candidate surface voxels have been considered (e.g., have been contacted or passed through). Alternatively, or in tandem, when no new sub-volume locations can be found for initial ball placement, the algorithm stops.

The spatial resolution of the surface depends on the diameter of the ball. While a small virtual ball provides greater resolution, it requires more time to construct a surface of the tissue wall. A large virtual ball provides lower resolution but constructs a surface of the tissue wall more quickly. Such a ball may be suitable for use with large cavities or a first round of construction, followed by a construction round with a smaller diameter ball. In an example, the diameter of the ball may be detected and the process presented to a user to decide whether or not to modify the diameter.

In some examples, the processor divides the volume of the image into a plurality of blocks and runs a virtual ball in each block. In this way, all of the balls can be operated concurrently (using parallel processing). The delineated surfaces of the respective blocks are connected when the process ends, so that the surface portions constructed in each of the blocks are combined to build the entire surface. In an example, the number and/or size of balls is user selected.

System Description

FIG. 1 is a schematic, pictorial illustration of a catheter-based ultrasound imaging system 20 using a catheter 21 with a distal end assembly 40 comprising a 2D ultrasound array 50 and a location sensor 52, in accordance with an example of the present disclosure. Integral location sensor 52 is preregistered with the 2D array 50 of catheter 21.

Specifically, sensor 52 is configured to output signals indicative of a position, direction and orientation of the 2D ultrasound transducer array 52 inside the organ. A processor of the system is configured to register multiple ultrasound image sections using the signal output by the sensor acquired by the 2D ultrasound transducer array 50, one with the other.

As seen, distal end assembly 40 is fitted at the distal end of a shaft 22 of the catheter. Catheter 21 is inserted through a sheath 23 into a heart 26 of a patient 28 lying on a surgical table 29. The proximal end of catheter 21 is connected to a control console 24. In the example described herein, catheter 21 is used for ultrasound-based diagnostic purposes, although the catheter may be further used to perform a therapy such as electrical sensing and/or ablation of tissue in heart 26, using, for example, a tip electrode 56.

Physician 30 navigates distal end assembly 40 of catheter 21 to a target location in heart 26 by manipulating shaft 22 using a manipulator 32 near the proximal end of the catheter.

In an example, 2D ultrasound array 50, shown in detail in an inset 25, is configured to image a left atrium of heart 26. The recorded images are stored by processor 39 in a memory 37.

As seen in an inset 45, ultrasound array 50 comprises a 2D array 50 of multiple ultrasound transducers 53. Inset 45 shows ultrasound array 50 navigated to an ostium wall 54 of a pulmonary vein of the left atrium. In this example, 2D array 50 is an array of 32×64 US transducers. The 2D array can image a section of the inner wall of the ostium. Because of the integral location sensor, the spatial coordinates of every pixel in the imaged section are known.

Control console 24 comprises a processor 39, typically a general-purpose computer, with suitable front end and interface circuits 38 for driving ultrasound transducers 53 (e.g., in a phased array manner that includes steering an ultrasound beam), and for receiving echo signals from transducers 53 for use by processor 39. Interface circuits 38 are further used for receiving signals from catheter 21, as well as for, optionally, applying treatment via catheter 21 in heart 26 and for controlling the other components of system 20. Console 24 also comprises a driver circuit 34, configured to drive magnetic field generators 36.

During the navigation of distal end 22 in heart 26, console 24 receives position and direction signals from location sensor 52 in response to magnetic fields from external field generators 36. Magnetic field generators 36 are placed at known positions external to patient 28, e.g., below table 29 upon which the patient is lying. These position and direction signals are indicative of the position and direction of 2D ultrasound-array 50 in a coordinate system of the position tracking system.

The method of position and direction sensing using external magnetic fields is implemented in various medical applications, for example, in the CARTO™ system, produced by Biosense Webster, which is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

In some examples, processor 39 may be configured to operate array 52 in an electronic "sweeping mode" to image a large portion of a cardiac camber. In an example, the ultrasound imaged cardiac chamber (e.g., a ventricle) is presented to physician 30 by processor 39 on a monitor 27, e.g., in as a volume rendering 55, where cavity 57 appearing in rendering 55 was reconstructed by processor 39 using the disclosed technique of constructing topography of a lumen wall as a 4D ultrasound image with a virtual ellipsoid or polyhedron, as further described in FIG. 2.

Processor 39 typically comprises a general-purpose computer which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise additional components and perform non-cardiac catheterizations. In particular, processor 39 runs a dedicated algorithm as disclosed herein, including in FIG. 4, that enables processor 39 to perform the disclosed steps, as further described below.

Constructing Topography of a Lumen Wall in a 4D Ultrasound Image with One or More Virtual Balls As noted above, in one example, a processor, such as processor 39, receives receiving a three-dimensional (3D) image of at least a portion of an organ including a cavity, the image comprising voxels having respective values. The processer identifies a wall of the cavity in the image, by applying the following steps to the image:

1. positioning one or more virtual solid objects of predefined sizes and shapes inside one or more respective sub-volumes of the cavity that are each enclosed within an interior of the cavity.
2. moving the one or more virtual solid objects inside the cavity according to a predefined rule of motion,
while the one or more virtual solid objects move inside the cavity, adapting the voxels that are traversed by the virtual solid objects to a predefined value indicative of the interior of the cavity.
3. in response to detecting that a virtual solid object comes into contact with a wall of the cavity, rolling the virtual solid object over the wall, and adapting a surface of the virtual solid object with the values of the voxels over which the surface rolls.
4. converting the adapted voxel values that are lower than a threshold voxel value into the predefined value indicative of the interior.

Figure 2A:
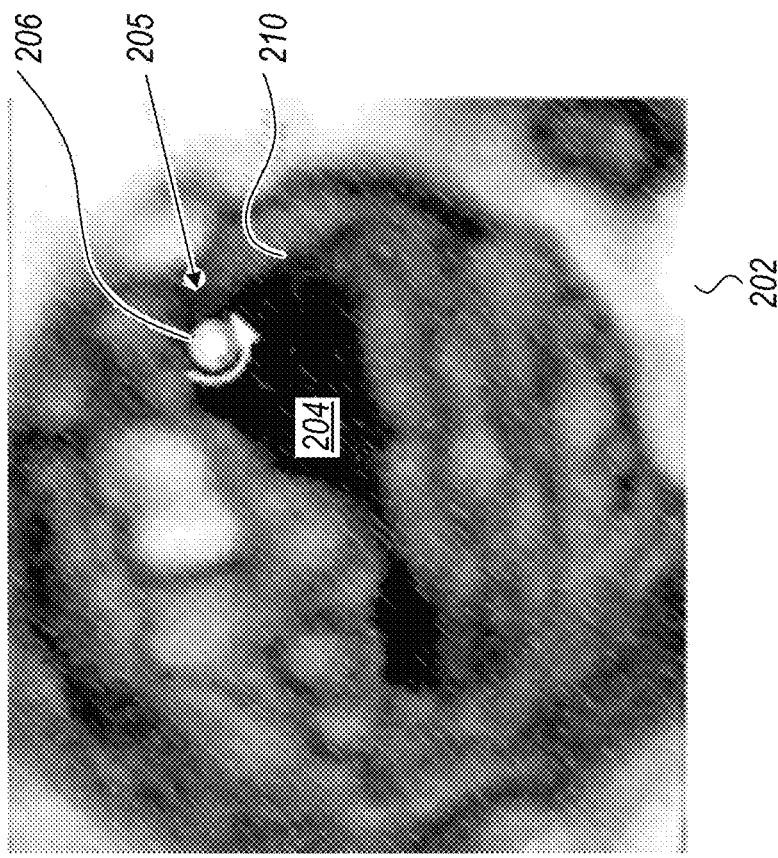
FIGS. 2A and 2B are schematic, pictorial illustrations of cavity construction by the disclosed image-processing technique applied to a 3D ultrasound image, in accordance with some examples of the present disclosure.
Figure 2B:
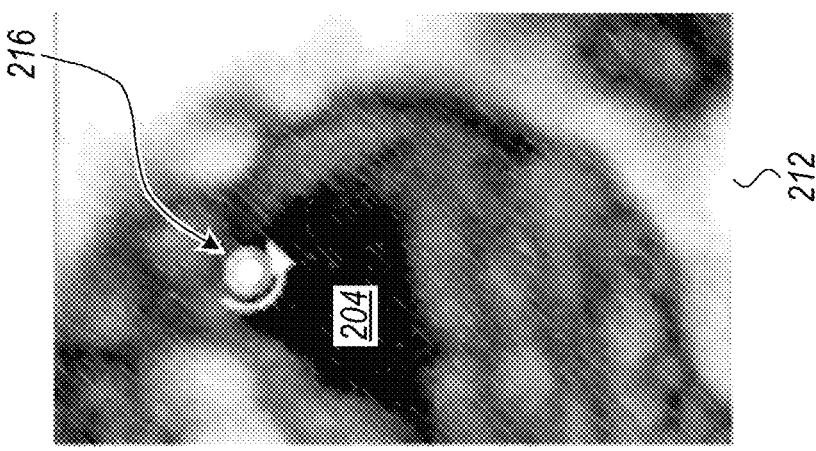
Figure 2B:
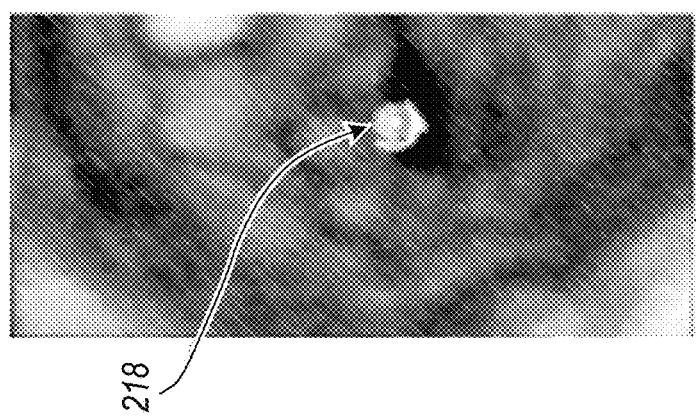

FIGS. 2A and 2B are schematic, pictorial illustrations of cavity construction by the disclosed image-processing technique applied to a 3D ultrasound image 202, in accordance with some examples of the present disclosure.

FIG. 2A shows a ball 205 of a given diameter, which, as it rolls over a cavity 204 wall 210, its surface 206 adapts voxel values (e.g., colors) of the cavity wall that it touches. It is noted that ball 205, may be entirely virtual, i.e., constructed within a virtual environment of the processing system for the purpose of generating a cleaner view to present on display for the physician and/or operator. In other words, the virtual ball may not be visible to a user on any display (although it could be, if desired). Thus, the depiction of the exemplary ball 205 in this disclosure should be considered primarily for the purpose of illustrating the technique of producing a cleaned view of the subject anatomy.

The rolling path may begin as a random, pseudo-random, or planned path. The surface of the virtual ball is "painted" with the image voxel values that it touches according to the following steps:

If the entire surface of the ball is black (not the case shown) the ball is situated in a portion of the 3D image that represents the lumen. The processor continues to move the ball and check the colors.

If the entire ball surface 206 (or part thereof) includes dispersed speckles of gray or white that do not form a continuous blob, the part of the ball that includes the dispersed speckles is still considered to be situated in a portion of the 3D image that represents the lumen. The processor accordingly changes all of the image voxels at that location to black. This cleans the "snow" noise due to blood flow. The processor then continues to roll the ball and check the colors.

If part of the surface of the ball includes a patch of white/gray, the patch is part of the tissue wall. The boundary is defined by setting a voxel threshold value so that a voxel value larger than the threshold means the voxel is part of the cavity wall tissue. The processor marks those tissue wall image voxels in white or with some other light shade of gray. The processor then changes the ball direction so that it bounces off of the detected tissue wall (not shown).

In FIG. 2B, which depicts an alternative or adjunct process to that just described, the processor divides the volume of image 202 into two blocks 212 and 214 and runs a virtual ball in each block. A large diameter ball 216 is used in the right larger image volume, while a smaller dimeter ball 218 is used in the smaller cavity volume. In this way, ball diameter can be optimized to the size of the portion of the volume. The smaller diameter ball is suited, for example, for smaller cavities, or for achieving higher surface resolution.

Moreover, since the two balls are operated concurrently (using parallel processing), this expedites cavity construction.

At the end of this procedure respective surfaces of blocks 212 and 214 are connected so that surface portions constructed in each of the blocks may be combined to build the entire surface.

Figure 3B:
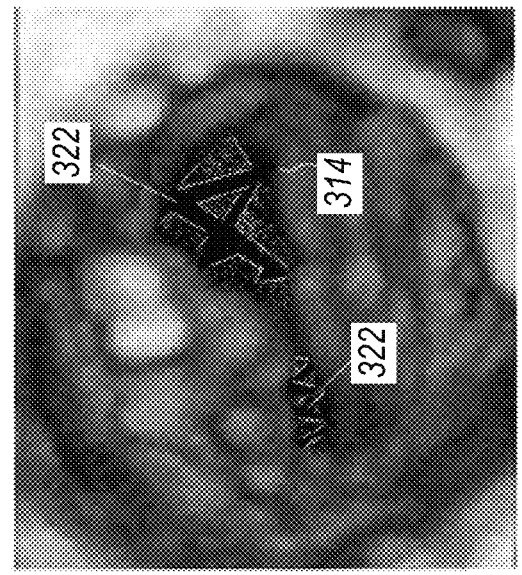
FIGS. 3A and 3B are schematic, pictorial illustrations of intermediate cavity construction by a shell and by bouncing paths, respectively, in accordance with some examples of the present disclosure.
Figure 3A:
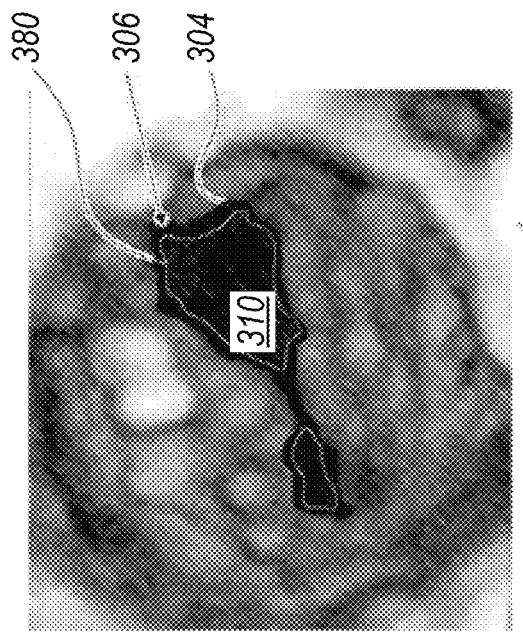

FIGS. 3A and 3B are schematic, pictorial illustrations of intermediate cavity construction 302 by a shell 306 and construction 312 by bouncing paths 322 (e.g., trajectories 322), respectively, in accordance with some examples of the present disclosure.

In FIG. 3A, a ball, such as ball 218 has been rolled over the cavity wall (e.g., wall 210) by processor 39 and as the ball rolls via (e.g., moved-through) cavity voxels, these adapt a predefined cavity voxel value (e.g., a color black). This creates a black shell 306 surrounding a reduced cavity 310 boundary 380. Next, the processor turns the color of each voxel of the reduced cavity 310 into black (i.e., converts values of all cavity voxels inner to shell 306 to the cavity voxel value), thereby achieving a fully distinct black cavity interfaced with a clearly delineated cavity wall surface 304.

In FIG. 3B, a ball bouncing off of the detected tissue walls was moving in paths 322 inside a cavity and had moved-through cavity voxels in paths 322 adapting a predefined cavity voxel value (e.g., a color black). In this example, the ball bounces between locations the ball hits (and adapts the color of the hit locations) over a cavity wall 314. The bouncing path may be along a planned path or one governed by a physical rule (e.g., specular reflection).

The construction steps described in FIGS. 2A and 2B and in FIGS. 3A and 3B were brought by way of example and are simplified for clarity of presentation. Additional or alternative steps may be performed, as described above.

Figure 4:
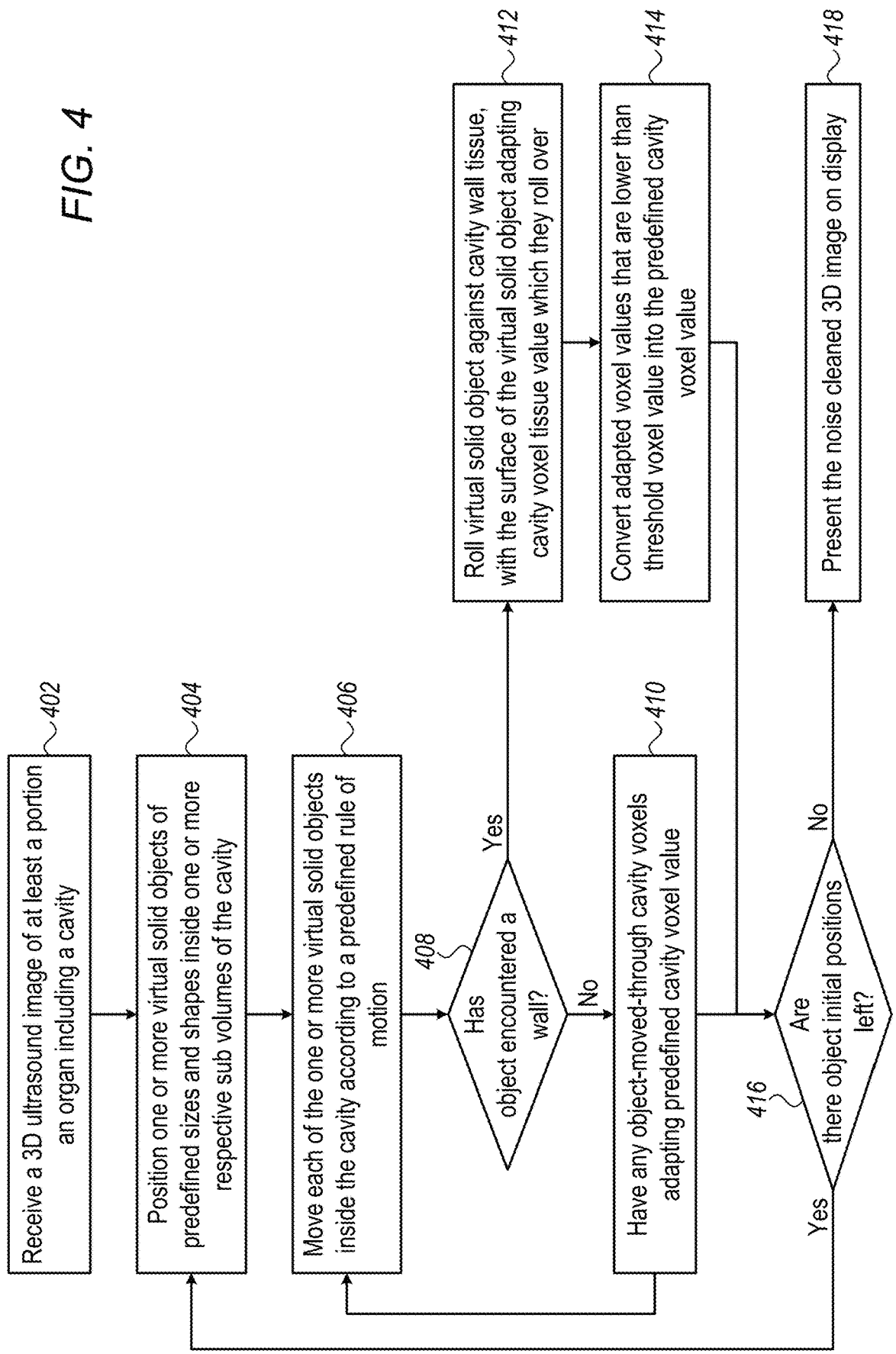
FIG. 4 is a flow chart that schematically illustrates a method for constructing a cavity by the disclosed image-processing technique applied to 3D ultrasound images, in accordance with an example of the present disclosure.

A Method of Constructing a Cavity in a 4D Ultrasound Image by Operating Virtual Objects FIG. 4 is a flow chart that schematically illustrates a method for constructing a cavity by the disclosed image-processing technique applied to 3D ultrasound images, in accordance with an example of the present disclosure. The algorithm according to the presented example carries out a process that begins with processor 39 receiving a 3D ultrasound image of at least a portion of an organ including a cavity, the image comprising voxels having respective values, at an 3D ultrasound image receiving step 402.

The processor runs the disclosed algorithm by positioning one or more virtual solid objects of predefined sizes and shapes inside one or more respective sub-volumes of the cavity that are each completely inside a volume known to be of the cavity (e.g., as shown in FIG. 2A or 2B), at virtual objects positioning step 404.

Next, processor 39 moves each of the one or more virtual solid objects inside the cavity according to a predefined rule of motion, such as having a linear trajectory and bouncing off a cavity wall with a specular direction (after rolling against a wall is completed) in a manner similar to the motion of billiard balls, at an object moving step 406. Alternatively, the processor may apply a random rule (e.g., a distribution of directions with probabilities, where a direction is randomly selected by the algorithm) to the bouncing direction off the cavity wall.

The processor regularly checks each object if it has encountered a wall, at a checking step 408.

If the answer is no, the one or more virtual solid objects move freely inside the cavity, and the processor has any moved-through cavity voxels adapting a predefined cavity voxel value, at a conversion to cavity voxel step 410, and the processor loops back to step 406.

If the answer is yes, i.e., once each of the one or more virtual solid objects comes in contact with a cavity wall, processor 39 rolls the virtual solid object against the cavity wall tissue, with the surface of the virtual solid object adapting cavity voxel tissue value over which they roll, at an object rolling step 412.

At voxel value conversion step 414, the processor converts adapted voxel values that are lower than a threshold voxel value into the predefined cavity voxel value, so as to reconstruct the cavity voxels with only the cavity voxel value.

At an end-criterion checking step 416, processor 39 checks if all initial positions (i.e., fully surrounded cavity locations) were used. If the answer is no, the processor returns to step 404. An alternative end-criterion checked in step 36 may be if all candidate surface voxels have been considered. If the answer is no, the processor returns to step 404.

If the answer is yes, the processor presents the 3D image, cleaned of noise, on a display that clearly shows the cavity and its wall, at a processed 3D ultrasound image presentation step 418.

The flowchart of FIG. 4 is brought by way of example. Images other than ultrasound images may be processed similarly (e.g., noisy CT images) to make cavities more visible. The construction method described in FIG. 4 was brought by way of example and is simplified for clarity of presentation. Additional steps, partial steps (e.g., only bouncing or only rolling), or alternative steps may be performed, as described above.

Example 1

A method includes receiving a three-dimensional (3D) image (202) of at least a portion of an organ including a cavity (204), the image comprising voxels having respective values. A wall (210) of the cavity in the image (202), is identified by applying the following steps to the image (i) positioning one or more virtual solid objects (205, 216, 218) of predefined sizes and shapes inside one or more respective sub-volumes of the cavity (204) that are each enclosed within an interior of the cavity, (ii) moving the one or more virtual solid objects (205, 216, 218) inside the cavity according to a predefined rule of motion, (iii) while the one or more virtual solid objects (205, 216, 218) move inside the cavity (204), adapting the voxels that are traversed (322) by the virtual solid objects to a predefined value indicative of the interior of the cavity, (iv) in response to detecting that a virtual solid object comes into contact with a wall of the cavity, rolling the virtual solid object over the wall (210), and adapting a surface (206) of the virtual solid object with the values of the voxels over which the surface (206) rolls, and (v) converting the adapted voxel values that are lower than a threshold voxel value into the predefined value indicative of the interior.

Example 2

The method according to example 1, wherein the predefined value indicative of the interior corresponds to a black color in the 3D image (202).

Example 3

The method according to any of examples 1 and 2, wherein the threshold voxel value corresponds to a color of a continuous bulb of predefined size of tissue of the wall (210) of the cavity (204).

Example 4

The method according to any of examples 1 through 3, wherein the predefined rule of motion specifies moving the one or more virtual solid objects (205, 216, 218) in linear trajectories (322) inside the cavity.

Example 5

The method according to any of examples 1 through 4, wherein the predefined rule of motion specifies bouncing the one or more virtual solid objects (205, 216, 218) off the wall (210) of the cavity (204) with a specular direction.

Example 6

The method according to any of examples 1 through 4, wherein the predefined rule of motion allows only rolling the one or more virtual solid objects (205, 216, 218) over the wall (210) of the cavity (204).

Example 7

The method according to any of examples 1 through 6, and comprising reconstructing the voxels belonging to the interior by defining a shell (306) along the wall (314), and converting the values of the voxels inner to the shell to the value indicative of the interior.

Example 8

The method according to any of examples 1 through 7, wherein the predefined rule of motion is random motion.

Example 9

The method according to any of examples 1 through 8, wherein the virtual solid object (304) is an ellipsoid.

Example 10

The method according to any of examples 1 through 8, wherein the virtual solid object (304) is a polyhedron.

Example 11

The method according to any of examples 1 through 10, wherein the 3D image (202) is a 3D ultrasound image.

Example 12

The method according to any of examples 1 through 11, wherein the cavity (204) is a cardiac cavity.

Example 13

The method according to any of examples 1 through 12, wherein the values of the voxels are given in Hounsfield units (HU).

Example 14

A system includes a memory (37) and a processor (39). The memory (37) is configured to store three-dimensional (3D) images (202). The processor (39) is configured to receive a 3D image (202) of at least a portion of an organ including a cavity (204), the image comprising voxels having respective values, and identify a wall (210) of the cavity in the image (202), by applying the following steps to the image (i) positioning one or more virtual solid objects (205, 216, 218) of predefined sizes and shapes inside one or more respective sub-volumes of the cavity (204) that are each enclosed within an interior of the cavity, (ii) moving the one or more virtual solid objects (205, 216, 218) inside the cavity according to a predefined rule of motion, (iii) while the one or more virtual solid objects (205, 216, 218) move inside the cavity (204), adapting the voxels that are traversed (322) by the virtual solid objects to a predefined value indicative of the interior of the cavity, (iv) in response to detecting that a virtual solid object comes into contact with a wall of the cavity, rolling the virtual solid object over the wall (210), and adapting a surface (206) of the virtual solid object with the values of the voxels over which the surface (206) rolls, and (v) converting the adapted voxel values that are lower than a threshold voxel value into the predefined value indicative of the interior.

Although the examples described herein mainly address cardiac applications, the methods and systems described herein can also be used in other body organs. For example, the disclosed technique may be used for ultrasound imaging of the stomach and bladder.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

receiving a three-dimensional (3D) ultrasound image of at least a portion of an organ including a cavity, the image comprising voxels having respective values; and identifying a wall of the cavity in the image, by applying the following steps to the image:

positioning one or more virtual solid objects of predefined sizes and shapes inside one or more respective sub-volumes of the cavity that are each enclosed within an interior of the cavity;

moving the one or more virtual solid objects inside the cavity according to a predefined rule of motion;

while the one or more virtual solid objects move inside the cavity, adapting pixel values of the voxels that are traversed by the virtual solid objects to a predefined value indicative of a color of the interior of the cavity;

in response to detecting that a virtual solid object comes into contact with a wall of the cavity, rolling the virtual solid object over the wall, and adapting pixel values of a surface of the virtual solid object to match pixel values of the voxels over which the surface rolls; and converting the adapted voxel values that are lower than a threshold voxel value into the predefined value indicative of the color of the interior.

2. The method according to claim 1, wherein the predefined value indicative of the interior corresponds to a black color in the 3D image.

3. The method according to claim 1, wherein the threshold voxel value corresponds to a color of a continuous bulb of predefined size of tissue of the wall of the cavity.

4. The method according to claim 1, wherein the predefined rule of motion specifies moving the one or more virtual solid objects in linear trajectories inside the cavity.

5. The method according to claim 1, wherein the predefined rule of motion specifies bouncing the one or more virtual solid objects off the wall of the cavity with a specular direction.

6. The method according to claim 1, wherein the predefined rule of motion allows only rolling the one or more virtual solid objects over the wall of the cavity.

7. The method according to claim 1, and comprising reconstructing the voxels belonging to the interior by defining a shell along the wall, and converting the values of the voxels inner to the shell to the value indicative of the interior.

8. The method according to claim 1, wherein the predefined rule of motion is random motion.

9. The method according to claim 1, wherein the virtual solid object is an ellipsoid.

10. The method according to claim 1, wherein the virtual solid object is a polyhedron.

11. The method according to claim 1, wherein the 3D image is a 3D ultrasound image.

12. The method according to claim 1, wherein the cavity is a cardiac cavity.

13. The method according to claim 1, wherein the values of the voxels are given in Hounsfield units (HU).

14. A system, comprising:

a memory configured to store three-dimensional (3D) ultrasound images; and a processor, which is configured to:

receive a 3D ultrasound image of at least a portion of an organ including a cavity, the image comprising voxels having respective values; and identify a wall of the cavity in the image, by applying the following steps to the image:

positioning one or more virtual solid objects of predefined sizes and shapes inside one or more respective sub-volumes of the cavity that are each enclosed within an interior of the cavity;

moving the one or more virtual solid objects inside the cavity according to a predefined rule of motion;

while the one or more virtual solid objects move inside the cavity, adapting pixel values of the voxels that are traversed by the virtual solid objects to a predefined value indicative of a color of the interior of the cavity;

in response to detecting that a virtual solid object comes into contact with a wall of the cavity, rolling the virtual solid object over the wall, and adapting values of a surface of the virtual solid object to match pixel values of voxels over which the surface rolls; and converting the adapted voxel values that are lower than a threshold voxel value into the predefined value indicative of the color of the interior.

15. The system according to claim 14, wherein the predefined value indicative of the interior corresponds to a black color in the 3D image.

16. The system according to claim 14, wherein the threshold voxel value corresponds to a color of a continuous bulb of predefined size of tissue of the wall of the cavity.

17. The system according to claim 14, wherein the predefined rule of motion specifies moving the one or more virtual solid objects in linear trajectories inside the cavity.

18. The system according to claim 14, wherein the predefined rule of motion specifies bouncing the one or more virtual solid objects off the wall of the cavity with a specular direction.

19. The system according to claim 14, wherein the predefined rule of motion allows only rolling the one or more virtual solid objects over the wall of the cavity.

20. The system according to claim 14, wherein the processor is further configured to reconstruct the voxels belonging to the interior by defining a shell along the wall, and converting the values of the voxels inner to the shell to the value indicative of the interior.

21. The system according to claim 14, wherein the predefined rule of motion is random motion.

22. The system according to claim 14, wherein the virtual solid object is an ellipsoid.

23. The system according to claim 14, wherein the virtual solid object is a polyhedron.

24. The system according to claim 14, wherein the 3D image is a 3D ultrasound image.

25. The system according to claim 14, wherein the cavity is a cardiac cavity.

26. The system according to claim 14, wherein the values of the voxels are given in Hounsfield units (HU).

* * * * *